(12) United States Patent
Moran et al.

(10) Patent No.: US 8,354,451 B2
(45) Date of Patent: Jan. 15, 2013

(54) TREATMENT OF MICROBIAL INFECTIONS WITH COMPOUNDS THAT INHIBIT 4-HYDROXYPHENYLPYRUVATE DIOXYGENASE

(75) Inventors: Graham R. Moran, Whitefish Bay, WI (US); Panqing He, Oak Creek, WI (US)

(73) Assignee: The UWM Research Foundation, Inc., Milwaukee, WI (US)

( * ) Notice: Subject to any disclaimer, the term of this patent is extended or adjusted under 35 U.S.C. 154(b) by 326 days.

(21) Appl. No.: 12/720,381

(22) Filed: Mar. 9, 2010

(65) Prior Publication Data

US 2010/0227936 A1     Sep. 9, 2010

Related U.S. Application Data

(60) Provisional application No. 61/158,471, filed on Mar. 9, 2009.

(51) Int. Cl.
*A61K 31/13*        (2006.01)
*A61K 31/135*      (2006.01)

(52) U.S. Cl. ......... 514/612; 514/645; 514/646; 514/657

(58) Field of Classification Search .................. 514/612, 514/645, 646, 657
See application file for complete search history.

(56) References Cited

OTHER PUBLICATIONS

Brownlee, J. et al., "Structure of the ferrous form of (4-hydroxyphenyl)pyruvate dioxygenase from *Streptomyces avermitilis* in complex with the therapeutic herbicide, NTBC," Biochem. (2004) 43:6370-6377.
Brownlee, J. et al., "Two roads diverged: the structure of hydroxymandelate synthase from *Amycolatopsis orientalis* in complex with hydroymandelate," Biochem. (2008) 47(7):2002-2013.
Conrad, J.A. et al., "The interaction of hydroxymandelate synthase with 4-hydroxyphenylpyruvate dioxygenase inhibitors," Inorganica Chimica Ada (2008) 361:1197-1201.
Gissen, P. et al., "Opththalmic follow-up of patients with tyrosinaemia type I on NTBC," J. Inherit Metab. Dis. (2003) 26:13-16.
He, P. et al., "We two alone will sing: the two-substrate a-keto acid-dependent oxygenases," Curr. Opin. Chem. Biol. (2009) 13:443-450.
Johnson-Winters, K. et al., "4-hydroxyphenyl)pyruvate dioxygenase from *Streptomyces avermitilis*: the basis for ordered substrate addition," Biochem. (2003) 42:2072-2080.
Johnson-Winters, K. et al., "Accumulation of multiple intermediates in the catalytic cycle of (4-hydroxyphenyl) pyruvate dioxygenase from *Streptomyces avermitilis*," Biochem. (2005) 44:7189-7199.
Kavana, M. et al., "Interaction of (4-hydroxyphenyl)pyruvate dioxygenase with the specific inhibitor 2-[2-nitro-4-(trifluoromethyl)benzoyl]-1,3-cyclohexanedione," Biochem. (2003) 42:10238-10245.
Lindblad et al., "The mechanism of enzymatic formation of homogentisate from p-hydroxyphenylpyruvate," J. Am. Chem. Soc. (1970) 92(25):7446-7449.
Moran, G.R., "4-hydroxyphenylpyruvate dioxygenase," Arch. Biochem. Biophys. (2005) 433:117-128.
Neidig, M.L. et al., "CD and MCD studies of the non-heme ferrous active site in (4-hydroxyphenyl)pyruvate dioxygenase: correlation between oxygen activation in the extradiol and alpha-KG dependent dioxygenases," J. Am. Chem. Soc. (2004) 126:4486-4487.
Neidig, M.L. et al., "Spectroscopic and computational studies of NTBC bound to the non-heme iron enzyme (4-hydroxyphenyl)pyruvate dioxygenase: active site contributions to drug inhibition," Biochem. Biophys. Res. Commun. (2005) 338:206-214.
Neidig, M.L. et al., "Spectroscopic and electronic structure studies of aromatic electrophilic attack and hydrogen-atom abstraction by non-heme iron enzymes," Proc. Natl. Acad. Sci. USA (2006) 103:12966-12973.
Nosanchuk et al., "Melanization of *Cryptococcus neoformans* in murine infection," Mol. Cell Biol. (1999) 19 (1):745-750.
Nunes, L.R. et al., "Transcriptome analysis of *Paracoccidioides brasiliensis* cells undergoing mycelium-to-yeast transition," Eukaryotic Cell (2005) 4(12):2115-2128.
Purpero, V. et al., "The diverse and pervasive chemistries of the alpha-keto acid dependent enzymes," J. Biol. Inorg. Chem. (2007) 12:587-601.
Purpero, V.M. et al., "Catalytic, noncatalytic, and inhibitory phenomena: kinetic analysis of (4-hydroxyphenyl) pyruvate dioxygenase from *Arabidopsis thaliana*," Biochem. (2006) 45:6044-6055.
Rundgren, M., "Steady state kinetics of 4-hydroxyphenylpyruvate dioxygenase from human liver (III)," J. Biol. Chem. (1977) 252:5094-5099.
Rundgren, M., "Tritium isotope effects in the reaction catalyzed by 4-hydroxyphenylpyruvate dioxygenase from *Pseudomonas* sp. Strain P.J. 874," Biochim. Biophys. Acta. (1982) 704(1):59-65.
Serre, L. et al., "Crystal structure of *Pseudomonas fluorescens* 4-hydroxyphenylpyruvate dioxygenase: an enzyme involved in the tyrosine degradation pathway," Structure Fold Des. (1999) 7:977-988.
Valeru et al., "A role of melanin pigment in *Vibrio cholerae* virulence expression factors," Infect. Immun. (2009) 77 (3):935-942.

*Primary Examiner* — Renee Claytor
(74) *Attorney, Agent, or Firm* — Michael Best & Friedrich LLP

(57) ABSTRACT

Methods of inhibiting phagolysosomal fusion in patients infected with a microorganism involve the administration of a 4-hydroxyphenylpyruvate dioxygenase (HPPD)-inhibiting compound, such as 2-(2-nitro-4-trifluoromethylbenzoyl)-1,3-cyclohexanedione (NTBC) to the patient. A HPPD-inhibiting compound administered in an amount effective to enhance phagolysosomal fusion in the macrophages or neutrophils of the patient reduces or treats the infection. Methods for treating bacterial infections by administering a HPPD-inhibiting compound and reducing the production of pyomelanin or melanin in microorganisms are disclosed.

10 Claims, 5 Drawing Sheets

A

NTBC

B

A

B

TREATMENT OF MICROBIAL INFECTIONS WITH COMPOUNDS THAT INHIBIT 4-HYDROXYPHENYLPYRUVATE DIOXYGENASE

CROSS REFERENCE TO RELATED APPLICATIONS

This application claims the benefit of priority to U.S. Provisional Application No. 61/158,471, filed Mar. 9, 2009, the entire disclosure of which is herein incorporated by reference for any purpose.

STATEMENT REGARDING FEDERALLY SPONSORED RESEARCH

This invention was made with US Government support awarded by National Institutes of Health, Grant No. DK59551 and The National Science Foundation, Grant No. MCB0843619. The United States government has certain rights in the invention.

INTRODUCTION

New methods of combating microbial infections would be useful to augment or replace traditional therapies such as antibiotics, particularly for infections that are slow to respond to, or are resistant to, traditional therapies.

SUMMARY OF THE INVENTION

In certain embodiments, a method for enhancing phagolysosomal fusion following infection of a patient with a microorganism comprises administering a composition comprising a 4-hydroxyphenylpyruvate dioxygenase (HPPD)-inhibiting compound, such as 2-(2-nitro-4-trifluoromethylbenzoyl)-1,3-cyclohexanedione (NTBC) to the patient in an amount effective to increase or enhance phagolysosomal fusion in the patient. The microorganism may be, for example, a fungus or a bacterium. Reduction in infection may manifest, for example, as a shortening in the time to recovery of the patient, and/or a reduction of the titer of the microorganism in the blood.

In certain embodiments, a method of reducing the production of or accumulation of melanin and/or pyomelanin in a microorganism may be carried out by exposing the microorganism to a HPPD-inhibiting compound, such as NTBC. The microorganism may be exposed, for example, by contacting the microorganism with the HPPD-inhibiting compound, or by administering a composition comprising the HPPD-inhibiting compound to a patient infected with the microorganism. In certain embodiments, the HPPD-inhibiting compound is administered in an amount effective to reduce the production and/or accumulation of melanin and/or pyomelanin by the microorganism. In certain embodiments, the administration of the 1,3-cyclohexanedione compound increases or enhances the ability of macrophages to attack and/or neutralize the microorganism by phagolysosomal fusion.

In certain embodiments, the HPPD-inhibiting compound, such as NTBC, is administered in a regime in combination with a second agent, such as an antibiotic or an antifungal.

In certain embodiments, a method for treating a patient suffering from a bacterial infection comprises administering a composition comprising a HPPD-inhibiting compound such as NTBC to the patient. The HPPD-inhibiting compound is administered in an amount effective to treat the infection.

DETAILED DESCRIPTION

Figure 1:
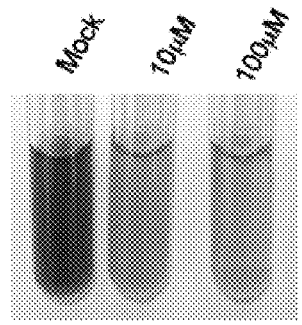
FIG. 1. NTBC decreases pigment production in *B. cenocepacia*. *B. cenocepacia* strains C5424 and MH1J were cultured in presence or absence of NTBC in flasks during 24 h. An aliquot of this culture was used to take the picture in A. To quantify pigment production, 1 ml of culture was centrifuged at 14,000 rpm by 5 min to pellet bacteria. The pigment in the supernatant was quantified at an OD597 nm. The graphic (B) was generated with the results of two independent experiments. Values represent the mean±SD of two independent experiments. ***, $p<0.001$, Mock (untreated) versus treated with 10 and 100 µM of NTBC.
Figure 1:
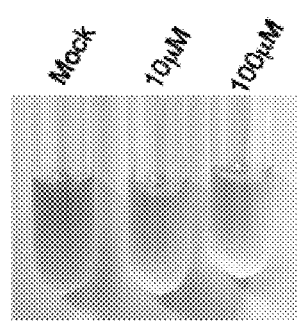
Figure 1:
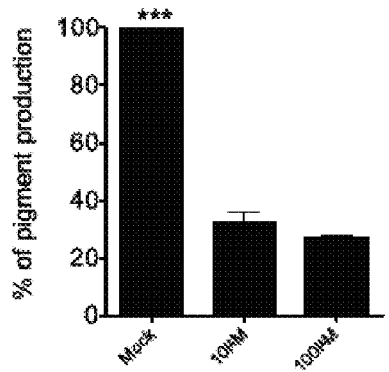
Figure 1:
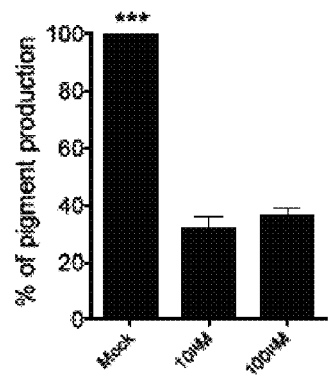

The present disclosure relates to methods of treating or inhibiting the progression of infection of a microorganism in a patient by administering a 4-hydroxyphenylpyruvate dioxygenase-inhibiting compound such as 2-(2-nitro-4-trifluoromethylbenzoyl)-1,3-cyclohexanedione (NTBC). NTBC is a triketone compound developed as a herbicide that has been used to treat the metabolic disorders, such as type I tyrosinemias, resulting from deficiencies in tyrosine catabolism.

Definitions and Usage of Terms

"Alkyl" refers to a saturated or unsaturated hydrocarbon chain having 1 to 18 carbon atoms, suitably 1 to 12 carbon atoms, or 1 to 6 carbon atoms, or 1 to 4 carbon atoms. "Lower alkyl" refers to a saturated or unsaturated hydrocarbon chain having 1 to 4 carbon atoms. Alkyl groups may be straight or branched. In some embodiments, branched alkyl groups have one or two branches. Unsaturated alkyl groups have one or more double bonds and/or one or more triple bonds. Suitably, unsaturated alkyl groups have one or two double bonds or one triple bond. Alkyl chains may be unsubstituted or substituted with from 1 to about 4 substituents unless otherwise specified. Suitably, alkyl groups are mono-, di-, or tri-substituted. Suitable alkyl substituents include, but are not limited to, cyano, halo, hydroxy, aryl (e.g., phenyl, tolyl, alkyloxphenyl, alkyloxycarbonylphenyl, halophenyl), heterocyclyl, and heteroaryl.

"Aromatic ring" or "aryl" refers to an aromatic hydrocarbon ring system. Aromatic rings are monocyclic or fused bicyclic ring systems. Monocyclic aromatic rings contain from about 5 to about 10 carbon atoms, suitably from 5 to 7 carbon atoms, or from 5 to 6 carbon atoms in the ring. Bicyclic aromatic rings contain from 8 to 12 carbon atoms, suitably 9 or 10 carbon atoms in the ring. Aromatic rings may be unsubstituted or substituted with from 1 to about 4 substituents on the ring. Suitable aromatic ring substituents include, but are not limited to, halo, cyano, lower alkyl, heteroalkyl, haloalkyl, phenyl, phenoxy or any combination thereof. Suitably, the aromatic ring substituents are lower alkyl, cyano, halo, or halo alkyl.

"Carbocycle" refers to a saturated or unsaturated hydrocarbon ring. Carbocycles are not aromatic. Carbocycles are monocyclic, or are fused, spiro, or bridged bicyclic ring systems. Monocyclic carbocycles contain from about 4 to about 10 carbon atoms, suitably from 4 to 7 carbon atoms, or from 5 to 6 carbon atoms in the ring. Bicyclic carbocycles contain from 8 to 12 carbon atoms, suitably from 9 to 10 carbon atoms in the ring. Carbocycles may be unsubstituted or substituted with from 1 to about 4 substituents on the ring. Suitable carbocycle substituents include, but are not limited to, halo, cyano, lower alkyl, heteroalkyl, haloalkyl, phenyl, phenoxy or any combination thereof. Suitably, the carbocycle substituents are halo or haloalkyl. Suitable carbocycles include, but are not limited to, cyclopentyl, cyclohexyl, cyclohexenyl, cycloheptyl, and cyclooctyl.

"Halo" or "halogen" refers to fluoro, chloro, bromo, or iodo.

"Haloalkyl" refers to a straight, branched, or cyclic hydrocarbon substituted with one or more halo substituents. Suitably, the haloalkyl is $C_1$-$C_{12}$, or $C_1$-$C_6$, or $C_1$-$C_3$. Suitable halo substituents include fluoro and chloro. One suitable haloalkyl is trifluoromethyl.

"Heteroalkyl" refers to a saturated or unsaturated chain containing carbon and at least one heteroatom, wherein no two heteroatoms are adjacent. Heteroalkyl groups contain from 1 to 18 member atoms (carbon and heteroatoms) in the chain, or 1 to 12 member atoms, or 1 to 6 member atoms, or 1 to 4 member atoms. Heteroalkyl groups may be straight or branched. Suitably, the branched heteroalkyl may have one or two branches. Unsaturated heteroalkyl have one or more double bonds and/or one or more triple bonds.

Suitably, heteroalkyl groups have one or two double bonds or one triple bond. Heteroalkyl groups may be unsubstituted or substituted with from 1 to about 4 substituents unless otherwise specified. Suitable heteroalkyl substituents include halo, aryl (e.g., phenyl, tolyl, alkyloxyphenyl, alkyloxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e g, amino, mono- and di-$C_1$-$C_3$ alkanylamino, methylphenylamino, methylbenzylamino, $C_1$-$C_3$ alkanylamido, carbamamido, ureido, guanidino).

"Heteroatom" refers to a nitrogen, sulfur, or oxygen atom. Groups containing more than one heteroatom may contain different heteroatoms. As used herein, halogens are not heteroatoms.

"Heterocycle" refers to a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocycles are not aromatic. Heterocycles are monocyclic, or are fused or bridged bicyclic ring systems. Monocyclic heterocycles contain from about 4 to about 10 member atoms (carbon and heteroatoms), suitably from 4 to 7 member atoms, or from 5 to 6 member atoms in the ring. Bicyclic heterocycles contain from 8 to 12 member atoms, suitably 9 or 10 member atoms in the ring. Heterocycles may be unsubstituted or substituted with from 1 to about 4 substituents on the ring. Suitably, the substituents are halo or haloalkyl. Suitable heterocycle substituents include: halo, cyano, lower alkyl, heteroalkyl, haloalkyl, phenyl, phenoxy or any combination thereof. Suitable heterocycles include, but are not limited to, piperzyl, morpholinyl, tetrahydrofuranyl, tetrahydropyranyl, and piperdyl.

"Heteroaryl" refers to an aromatic ring system containing carbon and from 1 to about 4 heteroatoms in the ring. Heteroaryls are monocyclic or fused bicyclic ring systems. Monocyclic heteroaryls contain from about 5 to about 10 member atoms (carbon and heteroatoms), or from 5 to 7 member atoms, or from 5 to 6 member atoms in the ring. Bicyclic heteroaryls contain from 8 to 12 member atoms, or 9 or 10 member atoms in the ring. Heteroaryls may be unsubstituted or substituted with from 1 to about 4 substituents on the ring. Suitable heteroaryl substituents include: halo, cyano, lower alkyl, heteroalkyl, haloalkyl, phenyl, phenoxy, or any combination thereof. Suitably, the substituents are halo, haloalkyl, or phenyl. Suitable heteroaryls include, but are not limited to, benzothienyl, benzofuranyl, thienyl, thiazolo, purinyl, pyrimidyl, pyridyl, and furanyl.

"Lower alkyl" refers to an alkyl chain comprised of 1 to 4 carbon atoms, suitably 1 to 3 carbon atoms or 1 to 2 carbon atoms. Lower alkyl groups may be saturated or unsaturated and substituted or unsubstituted. Lower alkyl groups include, but are not limited to, methyl, ethyl, propyl, isopropyl, butyl, isobutyl, and t-butyl.

"Lower heteroalkyl" refers to a heteroalkyl chain comprised of 1 to 4 member atoms. Lower heteroalkyl groups may be saturated or unsaturated and substituted or unsubstituted.

"Member atom" refers to a polyvalent atom (C, O, N, or S atom) in a chain or ring system that continues the chain or ring system. For example, in benzene the six carbon atoms are member atoms and the six hydrogen atoms are not member atoms.

"Phenyl" refers to a six-membered monocyclic aromatic ring which may or may not be substituted with from about 1 to about 4 substituents. The substituents may be substituted at the ortho, meta or para position on the phenyl ring, or any combination thereof. Suitable phenyl substituents include: halo, cyano, lower alkyl, heteroalkyl, haloalkyl, phenyl, phenoxy or any combination thereof.

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to 15 as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)$OCH_3$, —C(=O)$OCH_2CH_3$, —C(=O)OC($CH_3$)$_3$, and —C(=O)OPh.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)N($CH_3$)$_2$, —C(=O)$NHCH_2CH_3$, and —C(=O)N($CH_2CH_3$)$_2$. as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl Amino: —$NR^1R^2$, wherein $R^1$ and $R^2$ are independently amino substituents, for example, hydrogen, a $C_{1-7}$ alkyl group (also referred to as $C_{1-7}$alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —$NHCH_3$, —NHCH($CH_3$)$_2$, —N($CH_3$)$_2$, —N($CH_2CH_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Acylamido (acylamino): —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl.

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$heterocyclyl group, or a $C_{5-20}$ aryl group, preferably hydrogen or a $C_{1-7}$ alkyl group. Examples of ureido groups include, but are not limited to, —$NHCONH_2$, —NHCONHMe, —NHCONHEt, —$NHCONMe_2$, —$NHCONEt_2$, —$NMeCONH_2$, —NMeCONHMe, —NMeCONHEt, $NMeCONMe_2$, —$NMeCONEt_2$, and —NHCONHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)$CH_3$ (acetoxy), —OC(=O)$CH_2CH_3$, —OC(=O)C($CH_3$)$_3$, —OC(=O)Ph, —OC(=O)$C_6H_4$F, and —OC(=O)$CH_2$Ph.

Oxo: =O.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)$CH_3$ and —S(=O)$CH_2CH_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$$CH_3$ (methanesulfonyl, mesyl), —S(=O)$_2$$CF_3$, —S(=O)$_2$$CH_2CH_3$, and 4-methylphenylsulfonyl (tosyl).

Thioamido (thiocarbamyl): —C(=S)$NR^1R^2$, wherein $R^1$ and $R^2$ are independently amino substituents, as defined for amino groups. Examples of amido groups include, but are not limited to, —C(=S)$NH_2$, —C(=S)$NHCH_a$, —C(=S)N($CH_3$)$_2$, and —C(=S)$NHCH_2CH_3$.

Sulfonamino: —$NR^1$S(=O)$_2$R, wherein $R^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$$CH_3$, —NHS(=O)$_2$Ph and —N($CH_3$)S(=O)$_2$$C_6H_5$.

Other definitions include:

"Protected" refers to a chemical structure wherein one or more of the chemically-sensitive groups in the molecule have been modified to reduce its activity and allow for better synthetic techniques to be used. Protecting groups vary but are generally found in "Protecting Groups in Organic Synthesis" by Theadora Green.

"Unprotected" refers to a chemical structure that does not contain any groups that have been added to protect sensitive functional moieties such as hydroxy groups or carboxcylic acid groups.

HPPD-inhibiting compounds for use in the present invention include 2'-nitro-substituted benzoyl cyclohexanediones having the structure of Formula (I):

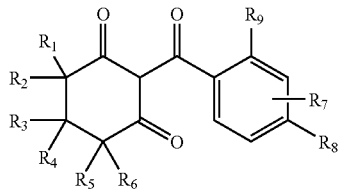

wherein $R_1$ and $R_3$-$R_6$ are hydrogen or alkyl, $R_2$ is hydrogen, alkyl or alkoxycarbonyl; $R_2$ is hydrogen or alkoxy; $R_8$ is hydrogen, halogen, alkoxy, alkyl, —$OCF_3$, cyano, nitro, haloalkyl (e.g. —$CF_3$), optionally substituted amino, optionally substituted aminosulfonyl, alkylcarbonyl, alkoxycarbonyl or $R_xS(O)_n$ wherein n is 0, 1 or 2 and $R_x$ is substituted alkyl, phenyl or benzyl; and $R_9$ is —$NO_2$, halogen, —$SO_2CH_3$, such as those disclosed in U.S. Pat. No. 5,006,158 to Carter et al., which is incorporated by reference herein. Exemplary compounds include those of Formula (II):

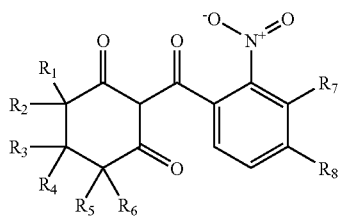

wherein $R_1$-$R_8$ are as defined above. 2-(2'-Nitro-4'-trifluoromethylbenzoyl)-1,3-cyclohexanedione (NTBC) is specifically contemplated.

Other exemplary inhibitors of HPPD include compounds such as isoxazoles (EP 418 175, EP 470 856, EP 487 352, EP 527 036, EP 560 482, EP 682 659, U.S. Pat. No. 5,424,276), for example, isoxaflutole, which is a herbicide selective for maize, diketonitriles (EP 496 630, EP 496 631), for example, 2-cyano-3-cyclopropyl-1-(2-$CH_3SO_2$-4-$CF_3$ phenyl)propan-1,3-dione and 2-cyano-3-cyclopropyl-1-(2-$CH_3SO_2$-4-2,3-C12 phenyl)propan-1,3-dione, triketones (EP 625 505, EP 625 508, U.S. Pat. No. 5,506,195), for example, sulcotrione or mesotrione, and pyrazolinates. The HPPD inhibitor may be chosen from diketonitriles, for example, 2-cyano-3-cyclopropyl-1-(2-$CH_3SO_2$-4-$CF_3$ phenyl) propan-1,3-dione and 2-cyano-3-cyclopropyl-1-(2-$CH_3SO_2$-4-2,3-C12 phenyl)propan-1,3-dione. The subject matter of each of the patents and applications referenced herein, which describe inhibitors of HPPD, is herein incorporated by reference.

In certain embodiments, methods of inhibiting 4-hydroxyphenylpyruvate dioxygenase (HPPD) in a microorganism, such as a pathogenic microorganism, by exposing the microorganism to an HPPD-inhibiting compound, such as NTBC, result in a reduction of the ability of the microorganism to infect the patient. In certain embodiments, the amount of melanin or pyomelanin, and/or homogentisate produced by a microorganism that has infected a patient may be reduced by exposing the microorganism to the HPPD-inhibiting compound in an amount effective to reduce the amount of melanin or pyomelanin in the microorganism. The microorganism may be exposed to the HPPD-inhibiting compound, for example, by contacting the microorganism with the HPPD-inhibiting compound, or by administering a composition comprising the HPPD-inhibiting compound to a patient infected with the microorganism. In certain embodiments, the HPPD-inhibiting compound is administered in an amount effective to inhibit or reduce the activity of HPPD or the amount of pyomelanin or melanin produced.

In certain embodiments, administration of a HPPD-inhibiting compound increases the susceptibility of the microorganism to one or more oxidative substances, for example, which may be synthesized by macrophages, or otherwise produced by the patient or host. Oxidative substances include for example, without limitation, hydrogen peroxide, hydroxyl radical, superoxide, peroxyl radical and combinations thereof.

Following infection of the patient, cells, such as macrophages or neutrophils, may exhibit reduced phagolysosomal fusion. Methods in which administration of an HPPD-inhibiting compound to the patient enhances phagolysosomal fusion in the patient may thereby facilitate treatment of the infection. The enhancement in phagolysosomal fusion may be evident compared with a similarly infected patient which has not had an HPPD-inhibiting compound administered. Following administration of the HPPD-inhibiting compound to a patient, the microorganism is prevented from effectively inhibiting phagolysosomal fusion, such that phagolysosomal fusion is enhanced.

The patient to be treated may be an animal, mammal, human, including, without limitation, animals classed as bovine, porcine, equine, canine, lupine, feline, murine, ovine, avian, piscine, caprine, corvine, acrine, or delphine.

The term "microorganism" as used herein may include any microorganism, whether naturally occurring or genetically engineered, and includes, for example, pathogenic microorganisms, such as pathogenic bacteria and pathogenic fungi. Exemplary microorganisms include viruses, eukaryotic microbes, bacteria, fungi, nanobacteria and parasites. Microorganisms include those which produce and/or accumulate melanin and/or pyomelanin. For example, Pseudomonas spp. (*Pseudomonas aeruginosa*), Legionella spp., *Vibrio* spp. (V cholera), *Cryptococcus* spp., *Aspergillus* spp. (*A. fumigatus*).

The infection to be treated may be, for example, a bacterial infection, or a fungal infection. In certain embodiments, the microorganism may become pathogenic, for example, by undergoing a morphological transition, or may become pathogenic upon infection of the patient in response to elevated temperatures in the patient.

Bacterial infections that may be treated include, without limitation, those caused by *Acetobacter aurantius, Acinetobacter baumannii, Actinomyces Israelii, Agrobacterium* spp. (*A. radiobacter, A. tumefaciens*), *Azorhizobium caulinodans, Azotobacter vinelandii, Anaplasma* spp. (*A. phagocytophilum, A. marginale*), *Bacillus* spp. (*B. anthracis, B. brevis, B. cereus, B. fusiformis, B. licheniformis, B. megaterium, B. mycoides, B. stearothermophilus, B. subtilis*), *Bacteroides* spp. (*B. fragilis, B. gingivalis, B. melaminogenicus* (now known as *Prevotella melaminogenica*)), *Bartonella* spp. (*B. henselae, B. quintana*), *Bordetella* spp. (*B. bronchiseptica, B. pertussis*), *Borrelia burgdorferi, Brucella* spp. (*B. abortus, B. melitensis, B. suis*), *Burkholderia* spp. (*B. mallei, B. pseudomallei, B. cepacia* complex, *B. cenocepacia*), *Calymmatobacterium granulomatis, Campylobacter* spp. (*C. coli, C. fetus, C. jejuni, C. pylori*), *Chlamydia* spp. (*C. trachomatis*), *Chlamydophila* spp. (*C. pneumoniae* (previously called *Chlamydia pneumoniae*), *C. psittaci* (previously called *Chlamydia psittaci*)), *Clostridium* spp. (*C. botulinum, C. difficile, C. perfringens* (previously called *Clostridium welchii*), *C. tetani*), *Corynebacterium* spp. (*C. diphtheriae, C. fusiforme*), *Coxiella bumetii, Ehrlichia chaffeensis, Enterobacter cloacae, Enterococcus* spp. (*E. avium, E. durans, E. faecalis, E. faecium, E. galllinarum, E. maloratus*), *Escherichia coli,*

*Francisella tularensis, Fusobacterium nucleatum, Gardnerella vaginalis, Haemophilus* spp. (*H. ducreyi, H. influenzae, H. parainfluenzae, H. pertussis, H. vaginalis*), *Helicobacter pylori, Klebsiella pneumoniae, Lactobacillus* spp. (*L. acidophilus, L. casei*), *Lactococcus lactis, Legionella pneumophila, Listeria monocytogenes, Methanobacterium extroquens, Microbacterium multiforme, Micrococcus luteus, Moraxella catarrhalis, Mycobacterium* spp. (*M. avium, M. bovis, M. diphtheriae, M. intracellulare, M. leprae, M. lepraemurium, M. phlei, M. smegmatis, M. tuberculosis*), *Mycoplasma* spp. (*M. fermentans, M. genitalium, M. hominis, M. penetrans, M. pneumoniae*), *Neisseria* spp. (*N. gonorrhoeae, N. meningitidis*), *Pasteurella* spp. (*P. multocida, P. tularensis*) *Peptostreptococcus, Porphyromonas gingivalis, Pseudomonas aeruginosa, Rhizobium Radiobacter, Rickettsia* spp. (*R. prowazekii, R. psittaci, R. quintana, R. rickettsii, R. trachomae*), *Rochalimaea* spp. (*R. henselae, R. quintana*), *Rothia dentocariosa, Salmonella* spp. (*S. enteritidis, S. typhi, S. typhimurium*), *Serratia marcescens, Shigella dysenteriae, Staphylococcus* spp. (*S. aureus, S. epidermidis*), *Stenotrophomonas maltophilia, Streptococcus* spp. (*S. agalactiae, S. avium, S. bovis, S. cricetus, S. faceium, S. faecalis, S. ferus, S. gallinarum, S. lactis, S. mitior, S. mitis, S. mutans, S. oralis, S. pneumoniae, S. pyogenes, S. rattus, S. salivarius, S. sanguis, S. sobrinus*), *Treponema* spp. (*T. pallidum, T. denticola*), *Vibrio* spp. (*V. cholerae, V. comma, V. parahaemolyticus, V. vulnificus*), *Wolbachia*, and/or *Yersinia* spp. (*Y. enterocolitica, Y. pestis, Y. pseudotuberculosis*).

Fungal infections that may be treated include, without limitation, those caused by *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigatus, Aspergillus niger, Blastomyces dermatitidis, Candida albicans, Candida glabrata, Candida guilliermondii, Candida krusei, Candida parapsilosis, Candida tropicalis, Candida pelliculosa, Cladophialophora carrionii, Coccidioides immitis, Cryptococcus neoformans, Cunninghamella* sp., *Epidermophyton floccosum, Exophiala dermatitidis, Filobasidiella neoformans, Fonsecaea pedrosoi, Fusarium solani, Geotrichum candidum, Histoplasma capsulatum, Hortaea werneckii, Issatschenkia orientalis, Madurella grisae, Malassezia furfur, Malassezia globosa, Malassezia obtusa, Malassezia pachydermatis, Malassezia restricta, Malassezia slooffiae, Malassezia sympodialis, Microsporum canis, Microsporum fulvum, Microsporum gypseum, Mucor circinelloides, Nectria haematococca, Paecilomyces variotii, Paracoccidioides brasiliensis, Penicillium marneffei, Pichia anomala, Pichia guilliermondii, Pneumocystis carinii, Pseudallescheria boydii, Rhizopus oryzae, Rhodotorula rubra, Scedosporium apiospermum, Schizophyllum commune, Sporothrix schenckii, Trichophyton mentagrophytes, Trichophyton rubrum, Trichophyton verrucosum, Trichophyton violaceum, Trichosporon asahii, Trichosporon cutaneum, Trichosporon inkin*, and/or *Trichosporon mucoides*.

The infection to be treated may be caused by a pigment-producing microorganism. Pigment producing bacteria include *Bordetella parapertussis, Borrelia burgdorferi, Corynebacterium diphtheriae, Enterococcus faecalis, Escherichia coli, Haemophilus influenzae, Legionella pneumophila, Listeria monocytogenes, Mycoplasma pneumoniae, Pseudomonas aeruginosa, Salmonella typhi, Salmonella typhimurium, Streptococcus agalactiae, Streptococcus pneumoniae, Vibrio cholerae*, and *Yersinia pestis*. Pigment producing fungi include *Aspergillus* spp., *Cryptococcus* spp., *Histoplasma* spp., *Pneumocystis* spp., *Stachybotrys* spp., and *Paracoccidioides* spp.

In certain embodiments, the patient is infected with a microorganism that causes a disease. Infectious diseases that may be treated, include, without limitation, Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis, Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus, Urinary Tract Infections, Aspergillosis, Blastomycosis, Candidiasis, Coccidioidomycosis, Cryptococcosis, Histoplasmosis, and/or Tinea pedis.

For treatment of the infection, or to enhance phagolysosomal fusion in the patient, such as in the macrophages and neutrophils of the patient, the HPPD-inhibiting compound should be administered in an effective amount. The HPPD-inhibiting compound may be, for example, administered to a patient in an amount of at least about 0.005 mg/kg/day, at least about 0.01 mg/kg/day, at least about 0.02 mg/kg/day, at least about 0.03 mg/kg/day, at least about 0.05 mg/kg/day, at least about 0.075 mg/kg/day, at least about 0.1 mg/kg/day, at least about 0.2 mg/kg/day, at least about 0.3 mg/kg/day, at least about 0.4 mg/kg/day, at least about 0.5 mg/kg/day, at least about 0.6 mg/kg/day, at least about 0.07 mg/kg/day, or at least about 0.08 mg/kg/day. The HPPD-inhibiting compound may be administered, for example, in an amount of less than about 150 mg/kg/day, less than about 125 mg/kg/day, less than about 100 mg/kg/day, less than about 90 mg/kg/day, less than about 80 mg/kg/day, less than about 70 mg/kg/day, less than about 60 mg/kg/day, less than about 50 mg/kg/day, less than about 40 mg/kg/day, less than about 30 mg/kg/day, less than about 20 mg/kg/day, less than about 10 mg/kg/day, less than about 8 mg/kg/day, less than about 5 mg/kg/day, less than about 4 mg/kg/day, less than about 3 mg/kg/day, or less than about 2 mg/kg/day.

Macrophage competition experiments may be used to establish the efficacy of a HPPD-inhibiting compound, for example, in phagolysosomal fusion. In a competition experiment, macrophages may be infected with a microorganism in vitro in the presence or absence of the HPPD-inhibiting compound and the amount of infection measured.

The amount of the HPPD-inhibiting compound administered may be sufficient to enhance phagolysosomal fusion in the patient, compared with a similarly infected patient not having been administered the HPPD-inhibiting compound. Phagolysosomal fusion may be enhanced, for example, by at least about 10%, at least about 20%, at least about 30%, at least about 40%, at least about 50%, at least about 60%, at least about 70%, at least about 80%, at least about 90%, at least about 100%, at least about 125%, at least about 150%, at least about 175%, at least about 200%, at least about 250%, at least about 300%, at least about 400%, at least about 500%, or at least about 1000%. Phagolysosomal fusion may be enhanced in one or more of macrophages and neutrophils in the patient.

The methods described herein, generally speaking, may be practiced using any mode of administration that is medically acceptable, meaning any mode that produces therapeutic levels of the active component of the HPPD-inhibiting compound, alone or in combination with a second agent, without causing clinically unacceptable adverse effects.

While it is possible for the HPPD-inhibiting compound to be administered alone, in some embodiments the active compound will be presented as a pharmaceutical composition (e.g., formulation) comprising at least one active form of the HPPD-inhibiting compound together with one or more pharmaceutically-acceptable carriers, adjuvants, excipients, diluents, fillers, buffers, stabilizers, preservatives, lubricants, or other materials well known to those skilled in the art and optionally other therapeutic or prophylactic agents.

Compositions may include one or more of the isoforms of a HPPD-inhibiting compound of the present invention. When racemates exists, each enantiomer or diastereomer may be separately used, or they may be combined in any proportion. Where tautomers exist, all possible tautomers are specifically contemplated.

Pharmaceutical compositions for use in accordance with the present invention may be formulated in a conventional manner using one or more physiologically acceptable carriers or excipients. Thus, the compounds may be formulated for administration by, for example, solid dosing, in a topical oil-based formulation, injection, inhalation (either through the mouth or the nose), implants, or oral, buccal, parenteral, or rectal administration.

Thus, pharmaceutical compositions and methods of making a pharmaceutical composition comprising admixing at least one active HPPD-inhibiting compound together with one or more pharmaceutically acceptable carriers, excipients, buffers, adjuvants, stabilizers, or other materials, are described herein.

The term "pharmaceutically acceptable" as used herein pertains to compounds, materials, compositions, and/or dosage forms which are, within the scope of sound medical judgment, suitable for use in contact with the tissues of a subject (e.g., patient, human or other animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Exemplary carriers, excipients, diluents etc. can be found in standard pharmaceutical texts, for example, Remington's Pharmaceutical Sciences, 18th edition, Mack Publishing Company, Easton, Pa., 1990. Pharmaceutically acceptable carriers and/or diluents include, for example, any and all conventional solvents, dispersion media, fillers, solid carriers, aqueous solutions, coatings, antibacterial and antifungal agents, isotonic and absorption delaying agents, and the like. Except insofar as any conventional media or agent is incompatible with the active HPPD-inhibiting compound or other active component, use thereof in the pharmaceutical compositions is contemplated. Supplementary active ingredients may also be incorporated into the compositions.

The formulations will conveniently be presented in unit dosage form and will be prepared by any method well known in the art of pharmacy. Such methods include the step of bringing into association the active compound with the carrier which constitutes one or more accessory ingredients. In general, the formulations will be prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations for oral administration (e.g., by ingestion) may be presented, for example, as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations for topical administration (e.g., transdermal, intranasal, ocular, buccal, and sublingual) may be formulated, for example, as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents. In addition, a formulation may be added to a conventional bandage, e.g. to a gauze portion that contacts the wound, as an antimicrobial agent.

Formulations for topical administration in the mouth include, for example, losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a liquid carrier.

Formulations for topical administration to the eye also include, for example, eye drops wherein the active compound is dissolved or suspended in a carrier, especially an aqueous solvent for the active compound.

Formulations for nasal administration, wherein the carrier is a solid, include, for example, a coarse powder having a particle size, for example, in the range of about 20 to about 500 microns which is administered in the manner in which snuff is taken, i.e., by rapid inhalation through the nasal passage from a container of the powder held close up to the nose. Nasal formulations wherein the carrier is a liquid for administration as, for example, nasal spray, nasal drops, or by aerosol administration by nebulizer, include, without limitation, aqueous or oily solutions of the active compound.

Formulations for administration by inhalation include, for example, those presented as an aerosol spray from a pressurized pack, with the use of a propellant, such as dichlorodifluoromethane, trichlorofluoromethane, dichoro-tetrafluoroethane, carbon dioxide, or other gases.

Formulations for topical administration via the skin include, for example, ointments, creams, and emulsions. When formulated in an ointment, the active compound may optionally be employed with either a paraffinic or a water-miscible ointment base. Alternatively, the active compound may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers include, for example, Tween 60, Span 80, cetostearyl alcohol, myristyl alcohol, glyceryl monostearate and sodium lauryl sulphate. The choice of oils or fats for the formulation may be based on achieving the desired cosmetic properties. Thus the cream may be a non-greasy, non-staining and washable product with a consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Formulations for rectal administration may be presented, for example, as a suppository with a suitable base comprising, for example, cocoa butter or a salicylate.

Formulations for vaginal administration may be presented, for example, as pessaries, tampons, creams, gels, pastes, foams or spray formulations containing in addition to the active compound, such carriers as are known in the art to be appropriate.

Formulations used for parenteral administration (e.g., by injection, including cutaneous, subcutaneous, intramuscular, intravenous and intradermal), include, for example, aqueous and non-aqueous isotonic, pyrogen-free, sterile injection solutions which may contain anti-oxidants, buffers, preservatives, stabilizers, bacteriostats in addition to the active compound, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Aqueous preparations may be formulated using dispersing or wetting agents and suspending agents. A sterile injectable preparation may be formulated as a sterile injectable solution or suspension in a nontoxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils may be employed as a solvent or suspending medium. For this purpose, any bland fixed oil may be employed including synthetic mono- or di-glycerides. In addition, fatty acids such as oleic acid may be used in the preparation of injectables. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In certain embodiments, the HPPD-inhibiting compound is orally administered.

Delivery systems may include, for example, sustained release delivery systems. Preferred sustained release delivery systems are those which can provide for release of the active component in sustained release pellets or capsules. Sustained release delivery systems include, but are not limited to: (a) erosional systems in which the active component is contain within a matrix, and (b) diffusional systems in which the active component permeates at a controlled rate through a polymer.

In certain embodiments, the HPPD-inhibiting compound is administered in therapeutically effective amounts. A therapeutically effective amount means that amount necessary at least partly to attain the desired effect, or to delay the onset of, inhibit the progression of, or halt altogether, the onset or progression of the infection being treated.

In certain embodiments, the HPPD-inhibiting compound is administered in conjunction or combination with one or more other therapeutic agents, for example in a treatment regime. The HPPD-inhibiting compound may be administered in a regime with at least one or more therapeutic agents. Therapeutic agents that may be co-administered with the HPPD-inhibiting compound include those, for example, that have antibacterial or antifungal effects, such as antibiotics and antifungals. Co-administration in a regime includes, for example, substantially simultaneous administration of the HPPD-inhibiting compound with the second agent in, for example, the same or different formulations. Co-administration may include, for example, separate administration of the HPPD-inhibiting compound and the second agent. The second therapeutic agent may include, without limitation, Ampicillin, Bacampicillin, Carbenicillin Indanyl, Mezlocillin, Piperacillin, Ticarcillin, Amoxicillin-Clavulanic Acid, Ampicillin-Sulbactam, Benzylpenicillin, Cloxacillin, Dicloxacillin, Methicillin, Oxacillin, Penicillin G, Penicillin V, Piperacillin Tazobactam, Ticarcillin Clavulanic Acid, Nafcillin, Cephalosporin I Generation, Cefadroxil, Cefazolin, Cephalexin, Cephalothin, Cephapirin, Cephradine, Cefaclor, Cefamandol, Cefonicid, Cefotetan, Cefoxitin, Cefprozil, Ceftmetazole, Cefuroxime, Loracarbef, Cefdinir, Ceftibuten, Cefoperazone, Cefixime, Cefotaxime, Cefpodoxime proxetil, Ceftazidime, Ceftizoxime, Ceftriaxone, Cefepime, Azithromycin, Clarithromycin, Clindamycin, Dirithromycin, Erythromycin, Lincomycin, Troleandomycin, Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, Pefloxacin, Imipenem-Cilastatin, Meropenem, Aztreonam, Amikacin, Gentamicin, Kanamycin, Neomycin, Netilmicin, Streptomycin, Tobramycin, Paromomycin, Teicoplanin, Vancomycin, Demeclocycline, Doxycycline, Methacycline, Minocycline, Oxytetracycline, Tetracycline, Chlortetracycline, Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole, Rifabutin, Rifampin, Rifapentine, Linezolid, Streptogramins, Quinopristin Dalfopristin, Bacitracin, Chloramphenicol, Fosfomycin, Isoniazid, Methenamine, Metronidazol, Mupirocin, Nitrofurantoin, Nitrofurazone, Novobiocin, Polymyxin, Spectinomycin, Trimethoprim, Colistin, Cycloserine, Capreomycin, Ethionamide, Pyrazinamide, Para-aminosalicyclic acid, Erythromycin ethylsuccinate, Miconazole, Ketoconazole, Clotrimazole, Econazole, Bifonazole, Butoconazole, Fenticonazole, Isoconazole, Oxiconazole, Sertaconazole, Sulconazole, Tioconazole, Fluconazole, Itraconazole, Isavuconazole, Ravuconazole, Posaconazole, Voriconazole, Terconazole, Terbinafine, Amorolfine, Naftifine, Butenafine, Anidulafungin, Caspofungin, Micafungin, Benzoic acid, Ciclopirox, Tolnaftate, Undecylenic acid, Flucytosine, or 5-fluorocytosine, Griseofulvin, Haloprogin and combinations thereof.

It will be apparent to those of skill in the art that variations may be applied to the compositions and methods described herein and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

It is to be understood that the invention is not limited in its application to the details of construction and the arrangement of components set forth in the following description. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The following non-limiting examples are purely illustrative.

EXAMPLES

Example 1

Demonstration that NTBC Decreases Pyomelanin Production in *B. cenocepacia*

To test the ability of NTBC 2-[2-nitro-4-(trifluoromethyl) benzoyl]-1,3-cyclohexanedione (NTBC) to decrease pigment production by *Burkholderia cenocepacia* strains, two strains with the ability to produce pigment were used: (i) the previously described *B. cenocepacia* C5424, and (ii) *B. cenocepacia* MH1J, strain with susceptibility to gentamicin. Both strains produce pigment but C5424 produces considerably more than MH1J as shown in FIG. 1A.

Bacteria were grown in 10 ml of Luria-Bertani (LB) broth at 37° C. with shaking, using 250 mL-flasks. *B. cenocepacia* C5424 produced significant pigment at 24 h of culture and MH1J required 48 h to form high pigment production. To quantify the pigment produced by both strains a 1 mL culture was taken at 24 hrs of incubation and the bacteria were pelleted by centrifugation at 14,000 r.p.m. for 5 min. The supernatants were then assayed by optical density at 597 nm (OD597).

In FIG. 1B, the percent of pigment production by both *B. cenocepacia* strains is shown. Pigment production in the presence of 10 μM and 100 μM NTBC was reduced to 31.95±3.96% and 26.89±0.59%, respectively, relative to the pigment production by untreated C5424 (FIG. 1B). Similarly, pigment production by MH1J in the presence of 10 μM and 100 μM of NTBC was reduced to 31.53±3.08% and 36.41±1.80% relative to the levels in untreated MH1J (FIG. 1B). Therefore, it can be concluded that NTBC has a significant inhibitory effect on pigment production.

Example 2

Effect of NTBC on Growth and Viability of *B. cenocepacia*

These experiments were done to test whether reduction of pigment production by NTBC was due to an effect of the inhibitor on viability and/or growth of the *B. cenocepacia* strains.

To assess growth rate, overnight cultures were inoculated into fresh medium with a starting optical density at 600 (OD600) of 0.1. Growth rates were determined in 100-well microtiter plates by use of a BIOSCREEN® C automated microbiology growth curve analysis system (MTX Lab Systems, Inc., Vienna, Va.) under high-amplitude shaking conditions.

Viability was tested by the LIVE/DEAD® method (Molecular probes, Invitrogen). 1 mL of bacterial culture was collected at 24 h, washed twice with phosphate buffered saline (PBS), and the pellet resuspended in 1 mL of Dubecco's modified Eagle's medium (DMEM) supplemented with 10% fetal bovine serum (FBS). Bacteria were incubated for 15 min at RT in the dark, 5 mL of the culture was used for fluorescence microscopy. Images were acquired using a QIMAGING® (Burnaby, British Columbia, Canada) cooled charge coupled-device camera on an Axioscope 2 (Carl Zeiss, Thornwood, N.Y.) microscope with an X100/1.3 numerical aperture Plan-Neofluor objective and a 50-W mercury arc lamp. Images were digitally processed using the Northern Eclipse version 6.0 imaging analysis software (Empix Imaging, Mississauga, Ontario, Canada).

Figure 2:
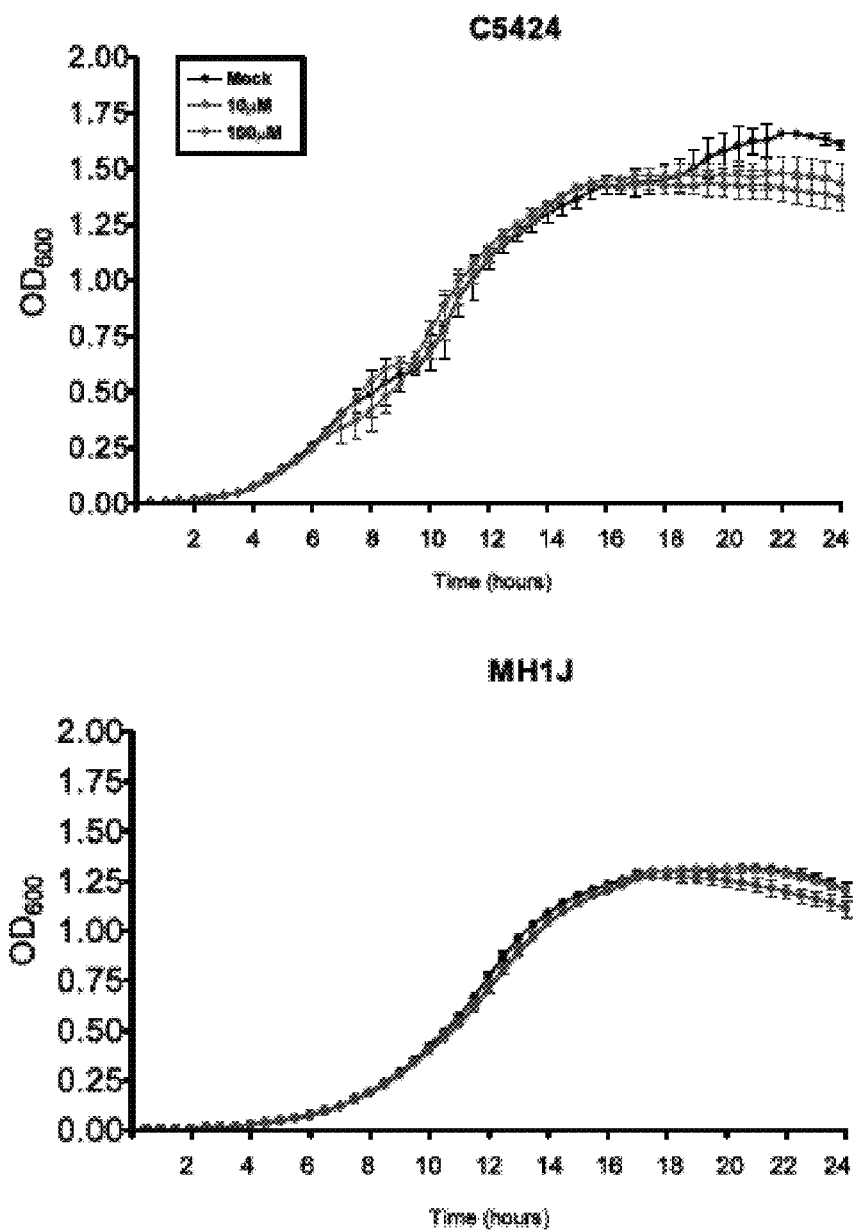
FIG. 2. Effect of NTBC on growth and viability of *B. cenocepacia*. *B. cenocepacia* C5424 (upper graph) and MH1J (lower graph) were cultured in 300 ml of LB by triplicates. Cultures were started at an OD600 of 0.1 and OD600 readings were taken every 30 min over 24 h using the BIOSCREEN® system.

*B. cenocepacia* C5424 and MH1J were cultured in the presence of 10 μM and 100 μM NTBC and assayed for growth rates using the BIOSCREEN® system (FIG. 2). Bacterial viability was examined under similar treatment conditions by fluorescence microscopy using the LIVE/DEAD® kit (Molecular Probes, Invitrogen). The results demonstrated that NTBC does not affect growth rate or viability.

Example 3

Quantitation of Macrophage Phagolysosomal Fusion in the Presence and Absence of NTBC A murine macrophage phagolysosomal fusion assay was developed to test the ability of macrophage cells to phagocytize bacteria in the presence and absence of NTBC. This study showed that pyomelanin secreted by microorganisms suppresses phagolysosomal fusion and that NTBC can halt the production of pyomelanin.

The murine macrophage-like cell line RAW 264.7 was obtained from the American type Culture Collection, Manassass, Va., USA, and routinely maintained in Dubecco's modified Eagle's medium (DMEM) supplemented with 10% FBS.

Macrophages were trypsinized and seeded into 6-well tissue culture plates containing glass cover slips. The cells were incubated overnight at 37° C., 5% $CO_2$ in DMEM medium supplemented with 10% FBS. Labeling of the endosomal pathway was performed by incubating the macrophages with dextran tetramethylrhodamine (10 000 MW) (TMR-dextran) at a final concentration of 250 μg/ml, for 2 h at 37° C. The external TMR-dextran was then removed by washing 3 times with pre-warmed PBS and then the media was refreshed and the microorganisms added.

Two samples were prepared that differed only in the inclusion or omission of NTBC. The microorganisms were grown for 36 h (or until pyomelanin was produced) and then washed twice with DMEM. The RAW 264.7 macrophage-like cells were then infected with the microorganism culture at a multiplicity of infection of 30. Infections were equalized by centrifugation at 1500 rpm for 1 min and were allowed to proceed for 2 hrs. After this period the external bacteria are removed by washing 3 times with RPMI-1640 media pre-warmed to 37° C.

Fluorescence and phase contrast images of the infected macrophage monolayers were acquired to establish the extent of microorganism acquisition by the macrophage cells using the LYSOTRACKER® dye that colocalizes with vacuoles that contain foreign cells. The percentage of phagolysosomal fusion was then determined from the number of stained and unstained vacuoles.

Figure 3:
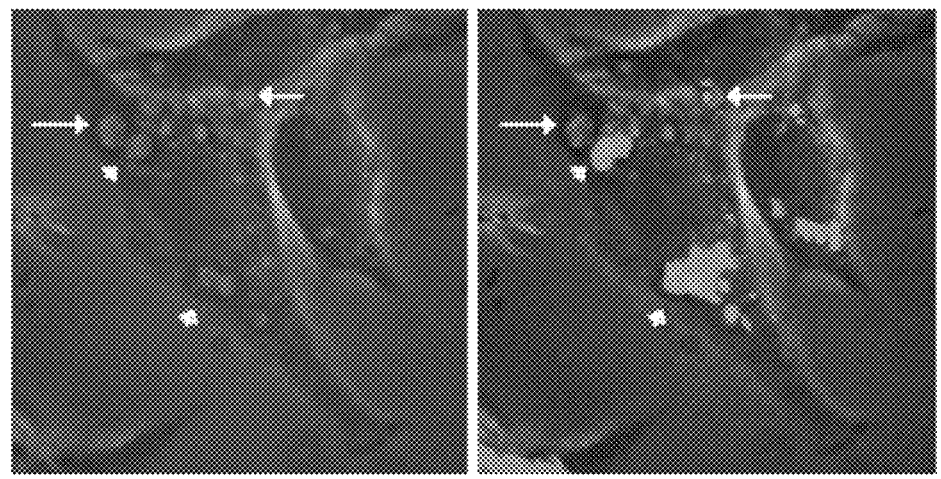
FIG. 3. Quantitation of phagolysosomal fusion of the BcCVs. RAW 264.7 macrophages were infected for 4 h with *B. cenocepacia* C5424 grown in presence or absence of NTBC, using an m.o.i. of 50. A. Macrophages were incubated with 1 µM LYSOTRACKER® Red-99 prior visualization. *B. cenocepacia* C5424 bacteria in membrane-bound vacuoles that do not colocalize with LYSOTRACKER® (arrows) and bacteria that colocalize with LYSOTRACKER® (arrowhead) are indicated. B. Percent of BcCV colocalizing with LYSOTRACKER® Red-99. The values correspond to the mean and SD of one experiment done in triplicate. **, $p<0.05$, macrophages infected with *B. cenocepacia* cultured in presence of 10 and 100 µM of NTBC versus non treated cells (Mock).
Figure 3:
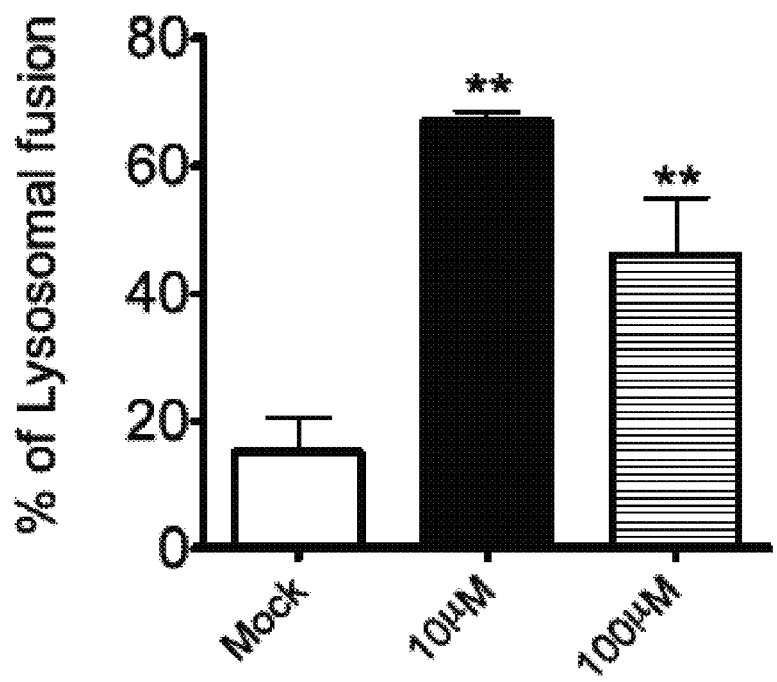
Figure 4:
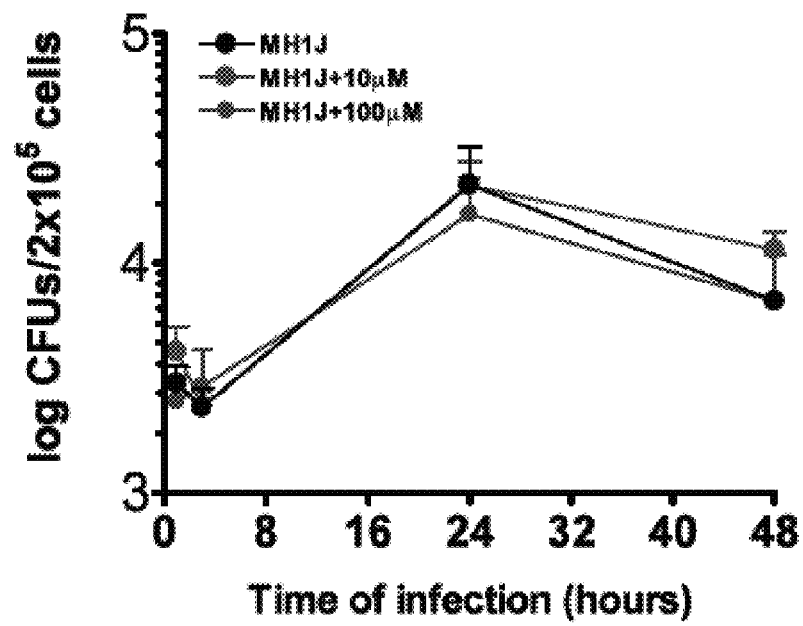
FIG. 4. Determination of intracellular killing of *B. cenocepacia* by macrophages treated with NTBC. RAW 264.7 cells were infected with *B. cenocepacia* strain MH1J for 1 h at 37° C. Extracellular bacteria were removed by centrifugation and infection was allowed to progress in the presence of gentamicin and with or without 10 and 100 µM of NTBC up to 48 h post-infection. Colony forming units (CFUs) were determined at 1, 3, 24 and 48 h. A, results using y-axis in logarithmic format. B, y-axis in linear format. The values correspond to the mean and SD of one representative experiment duplicated.
Figure 4:
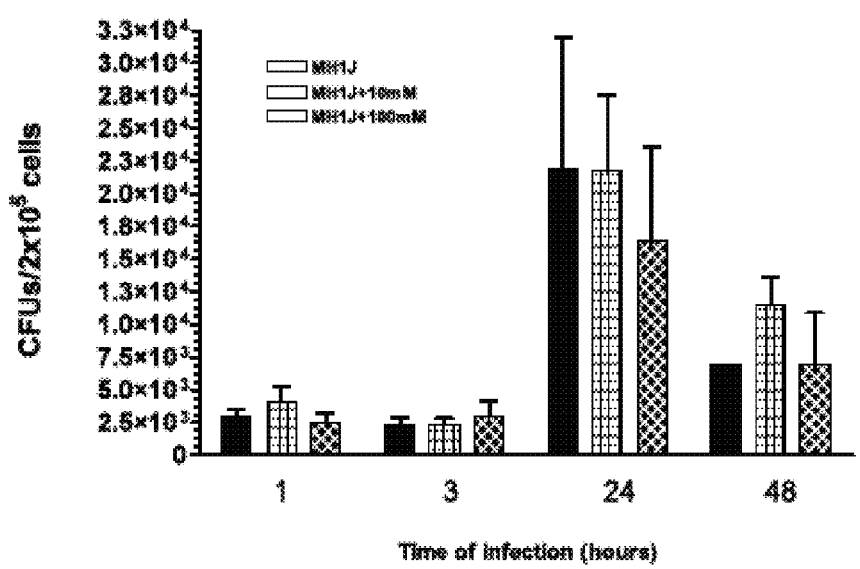

These results indicate that *B. cenocepacia* treated with inhibitor and therefore losing the ability to produce pigment display a significantly reduced ability to delay phagolysosomal fusion (FIG. 3).

Example 4

Determination of Intracellular Killing of *B. cenocepacia* by Macrophages Treated with NTBC The increased lysosomal fusion of BcCV in macrophages infected with *B. cenocepacia* grown in the presence of NTBC is evidence that intracellular bacteria may be more rapidly killed if exposed to NTBC after macrophage infection.

RAW264.7 macrophages were infected with *B. cenocepacia* MH1J, a derivative of J2135 with a deletion that causes gentamicin susceptibility (Hammad, H., unpublished) and intracellular bacteria were quantified by a gentamicin protection assay (4).

Infected macrophages were untreated or treated with NTBC (10 and 100 mM). Colony forming units (CFUs) were determined at 1, 3, 24 and 48 h post-infection. No differences were found in the treated vs. untreated macrophages (FIG. 4), suggesting that intracellular bacteria in macrophages cultured in the presence or absence of NTBC behave normally and survive and replicate slowly, as previously determined in our laboratory.

This experiment provides evidence that either NTBC cannot enter the macrophages or its effect is primarily on extracellular bacteria, which grow much more rapidly than intracellular bacteria (FIG. 4).

Example 5

Murine Model of Mammalian Infection

A murine model of systemic bacterial and fungal infection has been adopted in C57BL/6 mice. These mice exhibit a prominent macrophage and neutrophil inflammatory response when inoculated with microorganisms intraperitoneally. This response is a component of the defense mechanisms that will be augmented with the administration of NTBC.

Bacteria were grown in LB broth until mid log phase and sterile glycerol was added to 20% V/V and the cells were frozen at −80° C. Prior to experiments cells were thawed and revived for 2 hours at 37° C. with shaking. After revival, colony forming units were counted by plating to ensure that the inoculum was known.

The basis of the measurement was animal weight. Mice gain weight each day when fed ad libitum. Weight is therefore regarded a sensitive measure of the health of the animal. As such, observations were made for multiple days. In the first phase of the experiment, the inoculum required to ensure that the mice survive for 7-10 days was determined by intraperitoneal injection of bacteria over five orders of magnitude for five groups of mice. The inoculum that induced evidence of infection and permitted survival for 7-10 days was selected for subsequent trials of the test molecule.

Studies were performed on three groups of eight week old C57BL/6 black mice. Mice were housed on a 12-hr day/light cycle (beginning at 56 days of age) and allowed ad libitum access to food and water. Test and control mice were injected intraperitoneally with bacterial cells in 400 μL of LB Broth.

Test and negative control mice received dissolved NTBC daily at a rate of 1 mg/Kg by intraperitoneal injection.

The mice were observed and weighed daily. A general pathological examination was conducted at the time of sacrifice. Weight gain or loss was used as the primary indicator of infection or recovery. Mice were sacrificed if their weight decreased below 80% of their initial weight or after 10 days of observation.

Figure 5:
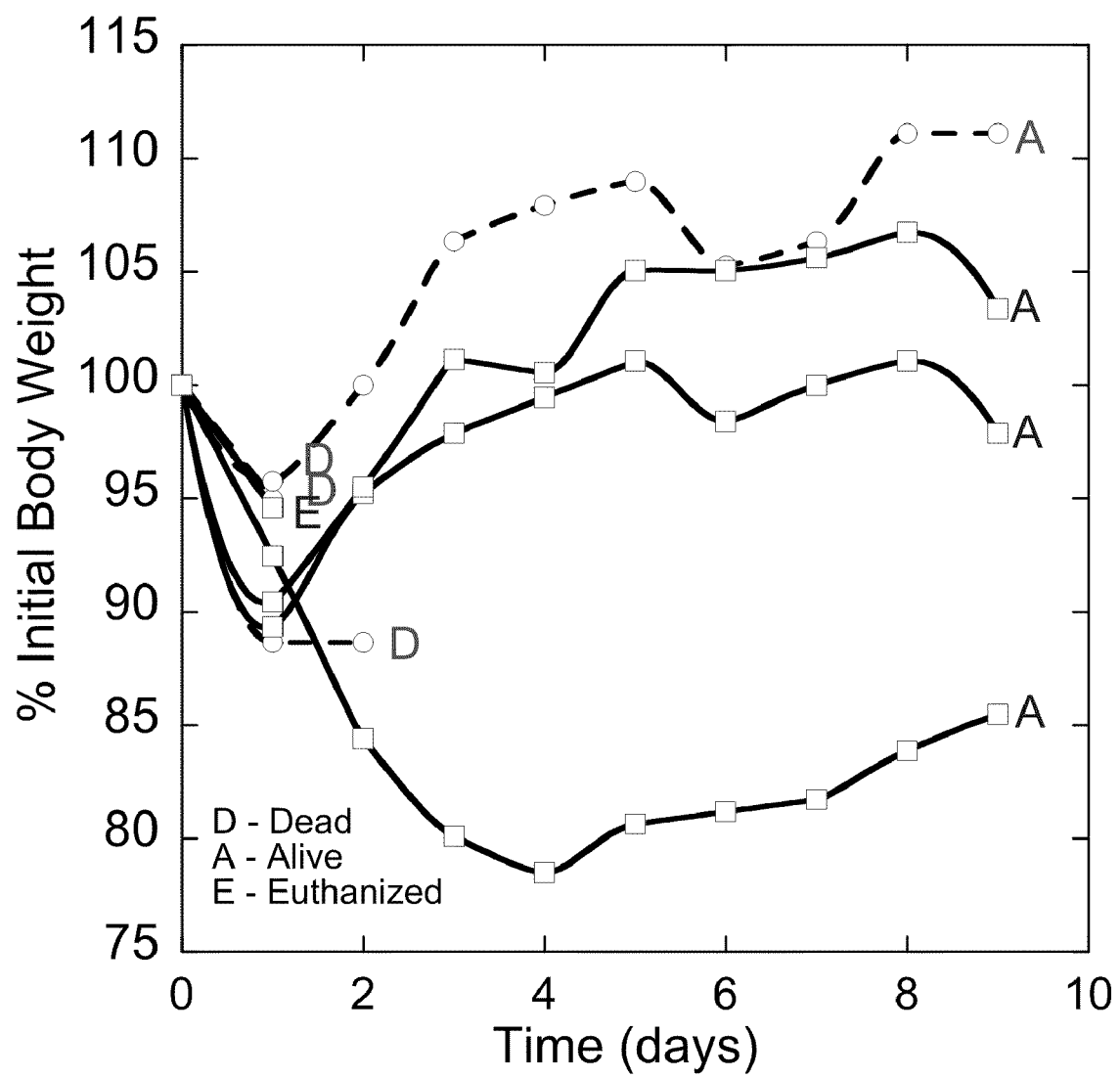
FIG. 5. Evidence of Efficacy of NTBC from C57BL/6 Mouse Infected Intraperitoneally with *Pseudomonas aeruginosa*. Eight week old mice were injected intraperitoneally with $3.2 \times 10^8$ colony forming units of *Pseudomonas aeruginosa*. The mice were separated into two groups, one that received only the pathogen (dashed lines) and another that was also given 1 mg/Kg NTBC daily by intraperitoneal injection (solid lines). Weights were recorded each morning.

The efficacy of the test compound is based on the growth and survival of the test group relative to that of the control. Continued growth by the test group above that observed in the control was taken of evidence of efficacy These data clearly show that mice treated with NTBC have a three-fold higher survival rate and return to normal growth within 24 hrs of administration of NTBC (FIG. 5).

Example 6

Murine Lung Infection Model

A murine model of bronchial infection is used that has been developed in C57BL/6 mice. This form of infection results in a chronic respiratory distress that is often persistent and difficult for the organism to eliminate effectively. This type of model is most appropriate to for organisms known to cause chronic and lethal lung infections such as *Pseudomonas* spp., *Burkholderia* spp., *Legionella* spp. and numerous fungi.

Bacteria are grown in LB broth until mid log phase. Sterile glycerol is added to 20% V/V and the cells frozen at −80° C. Prior to experiments, cells are thawed and revived for 2 hours at 37° C. with shaking. Colony forming units are counted by plating after revival to ensure that the inoculum is known.

The basis of the measurement is animal weight. As such, observations must be made for multiple days. In the first phase of the experiment, the inoculum required to ensure that the mice survive for 7-10 days is determined Microorganisms are deposited in the nasal cavity as concentrated droplets. The dose spans five orders of magnitude for five groups of mice. The inoculum that induces evidence of infection and permits survival for 7-10 days is selected for subsequent trials of the test molecule.

Studies are performed on three groups of eight week old C57BL/6 black mice. Mice are housed on a 12-hr day/light cycle and (beginning at 56 d of age) allowed ad libitum access to food and water. Test and control mice are inoculated nasally with microorganisms in 20 μL of growth medium. Test and negative control mice receive dissolved NTBC daily at a rate of 1 mg/Kg by intraperitoneal injection.

The mice are observed and weighed daily. A general pathological examination is conducted at the time of sacrifice. Weight gain or loss is used as the primary indicator of infection or recovery. Mice are sacrificed if their weight drops below 80% of their initial weight or after 10 days of observation. In general mice gain weight each day when fed ad libitum. Weight is thus seen a sensitive measure of the health of the animal.

The efficacy of the test compound is based on the growth and survival of the test group relative to that of the control. Continued growth by the test group above that observed in the control is expected and is taken of evidence of efficacy.

Example 7

A Murine Model of *Pseudomonas aeruginosa* Infection of the Eye

A murine model of eye infection will be developed in C57BL/6 mice using *P. aeruginosa*. This form of infection mimics the symptoms of the condition commonly known as "pink eye" where *P. aeruginosa* is the common causative agent.

Bacteria are grown in LB broth until mid log phase and sterile glycerol will be added to 20% V/V and the cells will then be frozen at −80° C. Prior to experiments cells are thawed and revived for 2 hours at 37° C. with shaking. Colony forming units are then determined by plating after revival to ensure that the inoculum is known.

The basis of the measurement is bacterial titer of the eye and observations will be made for multiple days. 20 μL of microorganism will be deposited in the left eye as concentrated droplets (~1×10$^7$ CFU).

Studies are performed on three groups of eight week old C57BL/6 black mice. The control group receives only the bacterial inoculum. The test groups are given the bacteria and NTBC: one group by intraperitoneal injection (1 mg/Kg) and the other as a 20 μL (5 mM) drop to the eye. Mice are housed on a 12-hr day/light cycle and (beginning at 56 d of age) allowed ad libitum access to food and water.

Bacterial titer of the eye will be the primary indicator of infection or recovery. 20 μL of tear is drawn each day, serially diluted onto LB Agar plates and grown at 32° C. for 20 hours. Bacterial colonies are counted and the test and control groups compared.

The efficacy of the test compound is based on the ability of the test group relative to that of the control to eliminate the bacteria from the infected eye. It is expected that the test groups will clear the bacteria at a rate that exceeds that of the control.

Example 8

A Murine Model of Antibiotic Resistant Microorganism Infection: NTBC as an Adjunct to Existing Antibiotics A murine model of systemic bacterial and fungal infection will be developed in C57BL/6 mice. The purpose of these studies is to demonstrate enhanced rates of recovery over and above that observed with common antibiotics when NTBC is used as an adjunct. These studies will use a variety of infectious microorganisms including but not limited to *P. aeruginosa, Salmonella typhimurium* and *B. cenocepacia*. Common antibiotics known to have widespread resistance will be tested such as ampicillin, tetracycline, and kanamycin.

Bacteria are grown in rich broth (appropriate to the organism) until mid log phase. Sterile glycerol is added to 20% V/V and the cells frozen at −80° C. Prior to experiments cells are thawed and revived for 2 hrs at 37° C. with shaking. After revival, colony forming units are counted by plating to ensure quantification of the inoculum.

The basis of the measurement is animal weight which is a sensitive measure of the health of the animal. Observations are made for multiple days. In the first phase of the experiment, the inoculum required to ensure that the mice survive for 7-10 days is established by intraperitoneal injection of bacteria over five orders of magnitude for five groups of mice. The inoculum that induces evidence of infection and permits survival for 7-10 days is selected for subsequent trials of the antibiotic and test molecule.

Mice are housed on a 12-hr day/light cycle and (beginning at 56 days of age) and allowed ad libitum access to food and water. For each combination of bacteria and antibiotic, three groups of eight week old C57BL/6 black mice are used. All test and control mice are injected intraperitoneally with the amount of bacteria determined as described above. The test and antibiotic control mice are given daily doses of the antibiotic at a rate of one half of the recommended dose by intraperitoneal injection. Test mice also receive dissolved NTBC daily at a rate of 1 mg/Kg by intraperitoneal injection.

The mice are observed and weighed daily. A general pathological examination is conducted at the time of sacrifice. Weight gain or loss is used as the primary indicator of infection or recovery. Mice are sacrificed if their weight decreases below 80% of their initial weight or after 10 days of observation.

The efficacy of the test compound is based on the growth and survival of the test group relative to that of the control and the antibiotic control. Growth of the test group above that observed in the control or the antibiotic control is expected as evidence of efficacy.

Example 9

Respiratory Infection Model using Squirrel Monkeys

A primate model for efficacy of NTBC in the treatment of infection will be developed in Juvenile Squirrel Monkeys. These studies will initially use intratracheal inoculation by *B. cenocepacia* and may be expanded to other bacterial and fungal pathogens.

Microorganisms are grown in rich broth until mid log phase, and colony forming units are counted by serial dilution and plating to ensure that the inoculum is known.

Healthy juvenile male squirrel monkeys weighing to 1.0 Kg are used. These animals are housed individually in wire cages and fed ad libitum commercial monkey chow and water. The monkeys are inoculated by placing sufficient inoculum in the trachea to induce a chronic lung infection that ultimately develops to a systemic infection.

The basis of the measurement is bacterial titer. As such, observations are made from dissected organs. In the first phase of the experiment, the inoculum required to ensure that the Monkeys survive for 2-4 days is established. Microorganisms are deposited in the trachea as concentrated droplets.

Studies are performed on two groups of monkeys. Test and control monkeys are inoculated with the pathogen. Test monkeys receive dissolved NTBC daily at a rate of 1 mg/Kg by intraperitoneal injection.

The Monkeys are euthanized at 6, 24, and 48 hours after infection with barbiturate. The thoracic cavity is opened aseptically and tissue samples of the major organs are removed. Each sample is weighed and homogenized in rich broth and brought to a volume of 4.0 mL. The slurry is then serially diluted and plated onto rich media agar plates and incubated for 10-15 hours. Colony counts permit the concentration of bacteria in the organs tested to be calculated.

The efficacy of the test compound is based on the microorganism load of the test group relative to that of the control. Evidence of elimination of the pathogen or lower titers in the test group will be taken of evidence of efficacy.

Example 10

Clinical Lab Testing

Clinical lab tests will initially use a cohort of cystic fibrosis patients identified as carrying a current *Pseudomonas* infection. This compromised group exhibits *Pseudomonas* in 50% of the cases in which mortality has resulted from the pathogenesis of microorganisms. NTBC is ostensibly non-toxic and has been used clinically, such that it can be added to existing therapies without significant risk to the patient.

Patients amenable to the treatment receive daily oral doses of solid NTBC at a rate of 1 mg/Kg. The progress of these patients is compared to that of a control group that receives only placebo in addition to their doctor recommended therapy.

NTBC is expected to undermine the ability of the microorganisms that produce pyomelanin or rely on 4-hydroxyphenylpyruvate dioxygenase activity for virulence to stave off the immune response of macrophage and neutrophil cells. Patients' immune responses should thus be enhanced and infections should exhibit shorter duration and severity.

We claim:

1. A method for treating a patient suffering from a bacterial infection, the method comprising administering a composition comprising 2-(2-nitro-4-trifluoromethylbenzoyl)-1,3-cyclohexanedione (NTBC) to the patient, the inhibitor being administered in an amount effective to treat the infection.

2. The method of claim 1, wherein the amount of NTBC administered is effective to reduce bacterial pyomelanin production.

3. The method of claim 1, wherein treating the infection comprises enhancing phagolysosomal fusion in the patient compared with a similarly infected patient not having been administered the inhibitor.

4. The method of claim 1, wherein the NTBC is administered in a regime in combination with an antibacterial agent.

5. The method of claim 1, wherein the infection is selected from a lung infection, an intestinal infection, cholera, pneumonia, septicemia, a urinary tract infection, a gastrointestinal infection, a skin infection and a soft tissue infection.

6. The method of claim 1, wherein the composition is administered orally.

7. The method of claim 1, wherein the bacterium is selected from *Bordetella parapertussis, Borrelia burgdorferi, Corynebacterium diphtheriae, Enterococcus faecalis, Escherichia coli, Haemophilus influenzae, Legionella pneumophila, Listeria monocytogenes, Mycoplasma pneumoniae, Pseudomonas aeruginosa, Salmonella typhi, Salmonella typhimurium, Streptococcus agalactiae, Streptococcus pneumoniae, Vibrio cholerae, Yersinia pestis, and Burkholderia cenocepaci.*

8. The method of claim 1, wherein the amount of NTBC administered is from 0.1 mg/Kg to 10 mg/Kg.

9. The method of claim 4, wherein the antibacterial agent is an antibiotic.

10. The method of claim 1, wherein the bacterium has a blood titer in the patient and wherein the blood titer of the bacterium is reduced following administration of the NTBC.

* * * * *